US00PP36675P2

(12) United States Plant Patent
Hansen

(10) Patent No.: US PP36,675 P2
(45) Date of Patent: May 13, 2025

(54) ***ALLIUM* PLANT NAMED 'Bobblehead'**

(50) Latin Name: ***Allium* hybrid (Linnaeus)**
Varietal Denomination: Bobblehead

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,336

(22) Filed: Nov. 22, 2024

(51) Int. Cl.
*A01H 5/02* (2018.01)
*A01H 6/04* (2018.01)

(52) U.S. Cl.
USPC ..... Plt./263.1
CPC ..... *A01H 6/04* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct cultivar of *Allium* ornamental onion plant named 'Bobblehead' has a large upright habit, with glaucous, stiff, broad, strap-like, upright, flattened, green foliage with longitudinal twisting. The numerous, tightly-clustered, pale lavender flowers forming a large, globose, upright umbel. The new plant is useful for containers, landscaping and cut flowers.

2 Drawing Sheets

Botanical classification: *Allium* hybrid (Linnaeus).
Variety denomination: 'Bobblehead'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Dec. 1, 2023, and the first offer for sale was on the same date. Subsequently, the new plant was advertised in the "Walters Gardens 2024-2025 Catalog" first mailed to customers on May 23, 2024. Walters Gardens, Inc. obtained the new plant and all information about the new plant directly from the inventor. No plants of *Allium* 'Bobblehead' have been sold or offered for sale in this country or anywhere in the world nor has any disclosure of the new plant been made more than one year prior to the filing date of this application and such sale or disclosure within one year was either derived directly or indirectly from the inventor.

BACKGROUND AND ORIGIN OF THE PLANT

The present invention relates to the new and distinct ornamental onion, *Allium* 'Bobblehead' was developed by the inventor at a wholesale perennial nursery in Zeeland, Michigan, USA as the result of a greenhouse cross of 'Serendipity' U.S. Plant Pat. No. 32,023 as the female or seed parent and 'Nor'easter' (not patented) as the male or pollen parent on Jun. 1, 2016. Seeds from this pollination were collected in autumn of 2016 and were sown later that same year. The individual plant was originally selected from all seedlings from this pollination in the summer of 2017 and was given the breeder code 16-3-8 during the remaining trial period.

*Allium* 'Bobblehead' has been successfully asexually propagated by division method since 2020 at a wholesale perennial nursery in Zeeland, Michigan, and was found to be stable and produce identical plants that maintain the unique characteristics of the original plant through multiple generations.

SUMMARY OF THE PLANT

*Allium* 'Bobblehead' differs from its parents as well as all other ornamental onion known to the applicant. The most similar known *Allium* cultivars known to the inventor are: 'Bubble Bath' U.S. Plant Pat. No. 35,333, 'Medusa' U.S. Plant Pat. No. 28,701, 'Millenium' (not patented), 'Pincushion' U.S. Plant Pat. No. 36,143, and 'Serendipity' U.S. Plant Pat. No. 32,023.

'Bubble Bath' has a slightly smaller habit with smaller umbels of softer lavender flowers. 'Medusa' has a smaller habit with smaller umbel heads of amethyst purple flowers. 'Millenium' has a smaller habit, darker rosy-purple flowers about two weeks later than the new plant with less-glaucous green leaves. 'Serendipity', the female parent, has a smaller habit, darker rosy-purple flowers on smaller umbel heads about two weeks later than the new plant. 'Nor'easter' has larger umbels of fewer umbels per clump, with a flower color that is a lighter lavender near white, and the leaves are broader.

*Allium* 'Bobblehead' differs from these above cultivars and all unregistered cultivars known to the inventor in the following combined traits:

1. Glaucous, upright, stiff, broad, strap-like, flattened, green foliage with longitudinal twisting;
2. Large habit, drought tolerant, rabbit and deer resistant clumps;
3. Numerous, tightly-clustered, pale lavender flowers forming a very large globose umbel;
4. Strong stems hold flower head globes upright through flowering and seed production.

BRIEF DESCRIPTION OF THE DRAWINGS

The photographs of the new plant demonstrate the overall appearance of the plant, including the unique traits growing in a trial garden at a nursery in Zeeland, Michigan. The colors are as accurate as reasonably possible with color reproductions. Ambient light spectrum, source and direction may cause the appearance of minor variation in color.

DETAILED BOTANICAL DESCRIPTION

Figure 1:
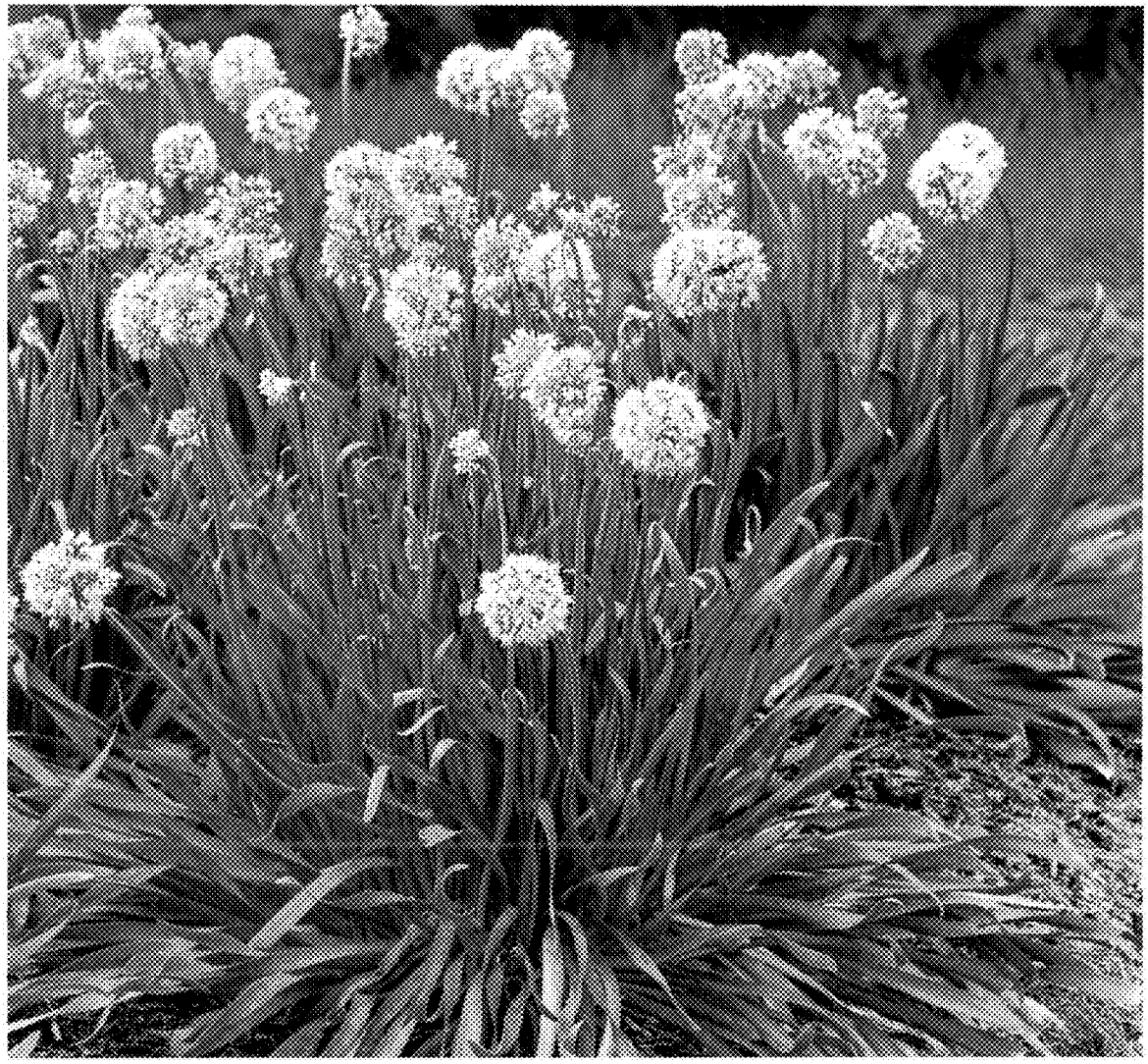
FIG. 1 shows the new plant habit of a three-year-old plant in early flowering in the foreground.
Figure 2:
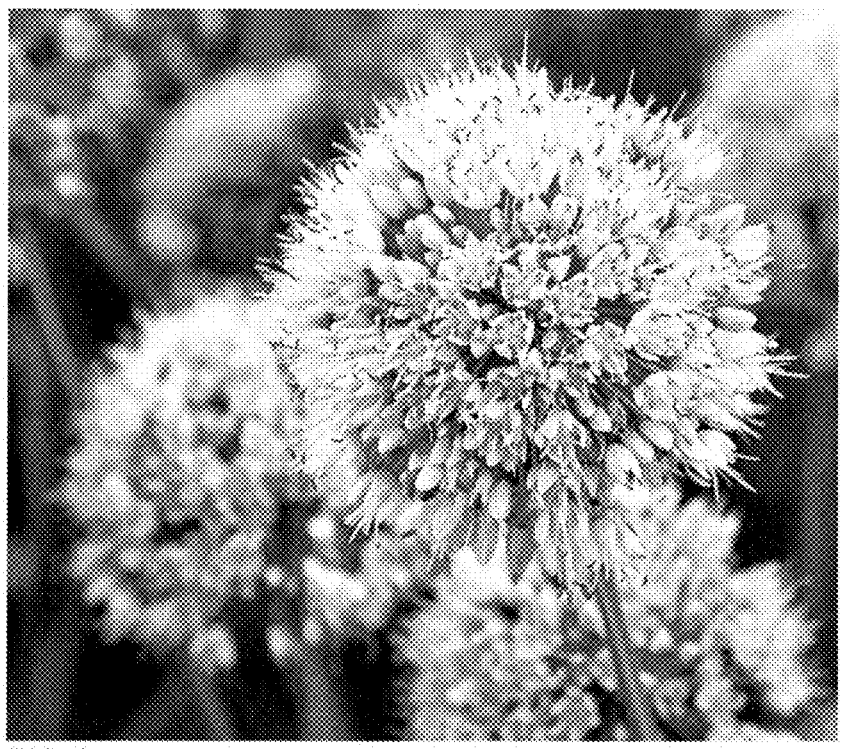
FIG. 2 shows a close-up of the umbel with flowers and buds.
Figure 3:
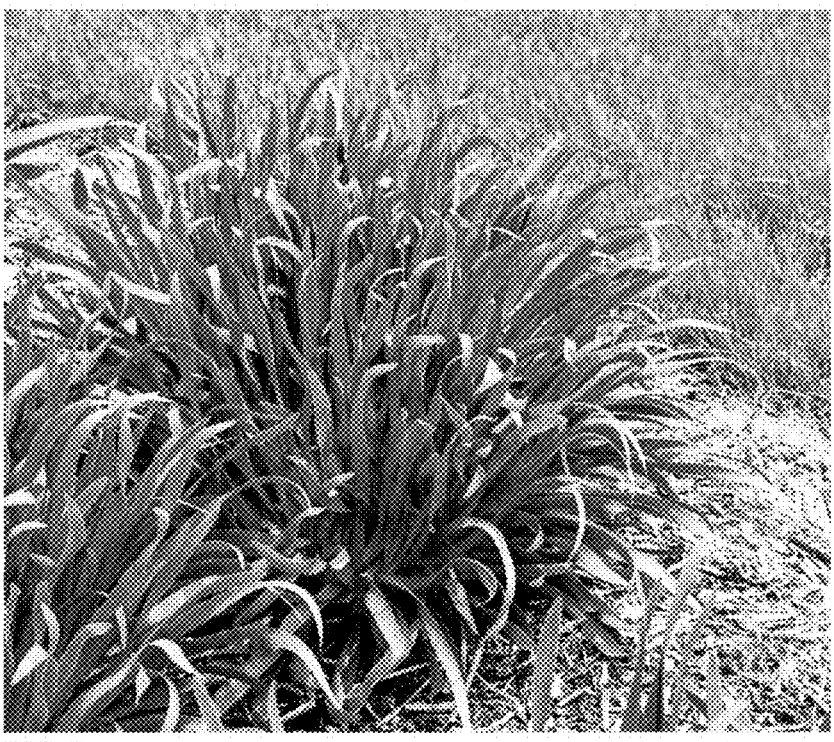
FIG. 3 shows a close-up of the foliage prior to flowering.

The following descriptions and color references are based on the 2015 edition of The Royal Horticultural Society Colour Chart except where common dictionary terms are used. The new plant, *Allium* 'Bobblehead', has not been observed under all possible environments. The phenotype may vary slightly with different environmental conditions, such as temperature, light, fertility, moisture, and maturity levels, but without any change in the genotype. The following observations and size descriptions are of a three-year-old plant in a display garden of a wholesale perennial nursery in Zeeland, Michigan under full sun with supplemental water and fertilizer as needed.

Botanical classification: *Allium* hybrid;

Parentage: Parent was 'Serendipity' as the female parent and 'Nor'easter' as the male parent;

Propagation method: By division;

Growth rate: Vigorous, flowering in 3.8-liter containers in about 12 weeks;

Rooting habit: Fibrous from base of bulbs, lightly branching; color nearest RHS 158C;

Plant habit description: Dense clump of bulbs with sessile rosulate foliage about 77 cm across and about 47 cm tall; about 45 inflorescences per plant; flowering to about 90 cm tall and inflorescences to about 78 cm across;

Bulbs: Elongated conical shape; about 7 cm long and 1.5 cm diameter at base; average about 42 per plant; color nearest RHS 155D;

Leaves: Sessile; linear; glaucous, glabrous, dull surfaces; semi-succulent; simple; margin entire; acute apex, truncate base; slightly twisted longitudinally around 360°; mostly flat; about 37 cm long, about 15 mm across near middle and to about 3.5 mm thick near middle; arranged in two-ranked tuffs from bulb; about 12 leaves per bulb; fragrance onion-scented;

Leaf color: Expanding adaxial and abaxial between RHS 138A and RHS N138C with base nearest RHS N144D; mature adaxial and abaxial between RHS N138B and RHS 137B distally with basal one-eighth transitioning to nearest RHS 145D;

Leaf venation: Parallel; color same as leaf abaxial and adaxial;

Inflorescence: In dense, terminal, globose umbel; about 250 to 300 flowers per inflorescence; about 9 cm across and about 8 cm tall; lasting about five weeks; beginning in mid-July to late August in Michigan;

Flower fragrance: Onion-like;

Blooming habit: One terminal umbel inflorescence per stem; with upright globe in bud, remaining upright as initial flowers open;

Buds one day prior to opening: Globose slightly flattened on three sides; rounded to truncate base, rounded apex; about 7 mm long and about 4 mm diameter at widest point near middle;

Bud color: Nearest RHS 76D;

Flowers: Campanulate; incomplete; perfect; with two sets of three tepals, outer set smaller than inner; superior ovary; actinomorphic; upward, outwardly, and drooping attitude depending on position in umbel; individually effective about four to six days; to about 12 mm long from base to exerted stamens and 12 mm across, corolla to about 12 mm across and 6 mm tall;

Tepals (outer set): Ovate to deltoid; convex; glabrous; lustrous; acute apex, fused truncate base; about 6 mm long and about 3 mm across;

Tepal (inner set): Ovate to deltoid; flat; glabrous; lustrous; acute apex, broadly acute base; about 7 mm long and to about 3.5 mm across;

Tepal color (inner and outer sets identical): Adaxial and abaxial nearly translucent to between RHS 84D, RHS 76D, and RHS NN155D;

Pedicel: Cylindrical; stiff; upward, and outwardly, and drooping depending on orientation in umbel; glabrous; glaucous; about 26 mm long and about 0.5 mm diameter;

Pedicel color: Between RHS 138A and RHS N138C;

Peduncle: Glabrous, glaucous; flattened trapezoid to nearly ovoidal with two wings in cross-section; to about 71 cm long, base about 9 mm wide and about 6 mm thick, middle portion about 10 mm wide and 7 mm thick;

Peduncle color: Basal 5 to 10 cm between RHS 145D and RHS 150D, middle portion between RHS 137A and RHS N138D, distally between RHS N138C and RHS 138A;

Gynoecium: Pistil single;

*Style*.—Single; cylindrical; glabrous; upon anthesis about 7 mm long and 0.5 mm diameter, lengthening to about 10 mm long and 0.5 mm across when mature; color between RHS 84D, RHS 76D, and RHS NN155D, maturing to nearest RHS N78D.

*Stigma*.—Acute; about 0.2 mm across; color nearest RHS NN155C.

*Ovary*.—Distinctly tri-locule; each locule rounded at apex and truncate base; nearly cylindrical; about 2.5 mm long and 2.5 mm across; color between RHS 84D, RHS 76D, and RHS NN155D at apex and nearest RHS NN155D at base.

Androecium: Typically, six; exserted to about 11 mm long;

*Anther*.—Oblong; about 2 mm long and about 1 mm wide; basifixed; longitudinal; color between RHS N187C and RHS N187D.

*Filament*.—Exserted; glabrous; cylindrical distally, flattened in proximal 3 mm; to about 8 mm long and 1 mm diameter at base and about 0.3 mm diameter below anther; color between RHS 84D, RHS 76D, and RHS NN155D distally and lightening to nearest RHS NN155D at base.

*Pollen*.—Abundant; color nearest RHS 189D.

Fruit: Tri-valved loculicidal capsule; about 6 mm wide and 4 mm tall; typically splitting to about 3 mm from base; each valve one to three seeded; color upon maturity nearest RHS 199D;

Seed: Prolific; elliptic, flattened along one long side; about 3 mm long and about 1.5 mm across; color nearest RHS 202A;

Disease and pest resistance: Ornamental onions typically resist deer and rabbit feeding. Resistance beyond that of other ornamental onions has not been observed.

*Allium* 'Bobblehead' plant grows best with good drainage and is able to tolerate some drought when established. Winter hardiness at least from USDA zone 4 through 8.

I claim:

1. A new and distinct cultivar of *Allium* plant named 'Bobblehead' as herein described and illustrated.

* * * * *